(12) United States Patent
Rivas

(10) Patent No.: US 7,400,257 B2
(45) Date of Patent: Jul. 15, 2008

(54) VITAL SIGNALS AND GLUCOSE MONITORING PERSONAL WIRELESS SYSTEM

(76) Inventor: Victor A. Rivas, P.O. Box 30711, Lincoln, NE (US) 68503

( * ) Notice: Subject to any disclaimer, the term of this patent is extended or adjusted under 35 U.S.C. 154(b) by 130 days.

(21) Appl. No.: 11/099,505

(22) Filed: Apr. 6, 2005

(65) Prior Publication Data

US 2006/0226991 A1  Oct. 12, 2006

(51) Int. Cl.
*G08B 23/00* (2006.01)
(52) U.S. Cl. ................. 340/573.1; 340/539.12; 600/300
(58) Field of Classification Search ............. 340/573.1, 340/539.11, 539.12, 870.16; 600/300
See application file for complete search history.

(56) References Cited

U.S. PATENT DOCUMENTS

| | | | |
|---|---|---|---|
| 2001/0044588 A1* | 11/2001 | Mault | 600/549 |
| 2002/0019584 A1* | 2/2002 | Schulze et al. | 600/300 |
| 2002/0109600 A1* | 8/2002 | Mault et al. | 340/573.1 |
| 2002/0118112 A1* | 8/2002 | Lang | 340/573.1 |
| 2003/0126593 A1* | 7/2003 | Mault | 725/10 |
| 2003/0208113 A1* | 11/2003 | Mault et al. | 600/316 |
| 2004/0130446 A1* | 7/2004 | Chen et al. | 340/539.13 |
| 2004/0147818 A1* | 7/2004 | Levy et al. | 600/300 |
| 2005/0165456 A1* | 7/2005 | Mann et al. | 607/30 |

OTHER PUBLICATIONS

Cline, Gary W. et al.; *Impaired Glucose Transport as a Cause of Decreased Insulin-Stimulated Muscle Glycogen Synthesis in Type 2 Diabetes*; The New England Journal of Medicine; July 22, 1999; vol. 341, No. 4; pp. 240-246.
Anon.; *Philips Electronics to Develop Broadband Devices for French Market*; Appliance; Jan. 2004; p. 16.
Anon.; *TMIO Product Named Coolest Invention by Time Magazine*; Appliance; Jan. 2004; p. 6.
Rupley, Sebastian; *Calling the Web: Smart Phones get Smarter*; PC Magazine; Dec. 14, 1999; p. 32.
Braukus, Michael; *NASA Joins Diabetes Fight*; Aerospace Technology Innovation(http://nctn.hq.nasa.gov; p. 8.
Anon.; *Wireless Sensors Chat Together*; Electronic Design (PlanetEE.com); Aug. 18, 2003; p. 11.
Couzin, Jennifer: *Prescription: Plenty of bed rest and a gold microchip*; U.S. News & World Report; Jul. 5, 1999; p. 55.
Scanlon, Jessie; *Digital Eyes Peg Skin Cancer*; Popular Science; May 2004; p. 66.

* cited by examiner

*Primary Examiner*—Thomas J Mullen, Jr.
(74) *Attorney, Agent, or Firm*—James Creighton Wray; Clifford D. Hyra

(57) ABSTRACT

Medical monitoring technologies are integrated with wireless networks to wirelessly send signals from a monitoring device to a cellular telephone or other personal electronic device (PED). A sensor is placed inside or on the patient's body. Information from the monitoring sensor is transmitted to a nearby and/or remote PED. The information transmitted to the PED may then be displayed, processed, stored or forwarded to another location if needed. The monitoring system of the present invention monitors a variety of bodily processes, but preferably measures vital signals such as heart rate, blood pressure, respiration rates, etc. The present invention may also be used to monitor glucose levels in diabetic users. Further, the device may be used as an alert system to alert the patient and third parties when a patient experiences an adverse medical condition.

38 Claims, 6 Drawing Sheets

VITAL SIGNALS AND GLUCOSE MONITORING PERSONAL WIRELESS SYSTEM

BACKGROUND OF THE INVENTION

Adverse medical conditions may lead to long-term illness effects or even death. Often, the warning signs of adverse medical conditions are not recognized in time to take preventative measures. The lack of notice can lead to severe long-term effects for conditions such as heart conditions. Other conditions, such as diabetes require frequent and continued monitoring to prevent dangerous effects.

The severity of problems caused by adverse medical effects can be mitigated by early detection of the condition and subsequent treatment. Early detection systems are available, but suffer from limitations on ease of use and practicability. Existing monitoring systems utilize heavy or awkward technology that must be connected directly to a patient. The patient must be in close proximity to the monitoring technology in order for monitoring to occur through wires. Other technology may be carried around by a patient, but is still bulky and restricts movement.

Needs exist for improved early detection and monitoring systems for adverse medical conditions that provide continuous monitoring and allow a patient mobility.

In recent years, the availability and performance of wireless computer networks has increased exponentially. The popularity of cellular telephones and other wireless information devices, such as laptop computers, Palm Pilots, global positioning systems, and other personal electronic devices increases every day. Increases in performance coupled with decreases in prices have made wireless networks available to a large part of the population.

Current medical monitoring systems do not adequately utilize wireless technologies to provide real-time monitoring of medical conditions with patient mobility.

Needs exist for monitoring methods that combine early detection and monitoring of adverse medical conditions with wireless technology.

SUMMARY OF THE INVENTION

The present invention integrates medical monitoring technologies with wireless networks to wirelessly send signals from a monitoring device on a patient to a cellular telephone or other personal electronic device (PED). A thin, lightweight, flexible monitoring sensor or sensor chip is placed inside or on the patient's body. Information from the monitoring sensor is transmitted by wireless or infrared technology to a nearby and/or remote cellular telephone or other personal electronic device. By placing the heavier, bulkier components of the monitoring system for comparing, recording, altering and transmitting in the cellular telephone or other personal electronic device, the patient is freed from the restriction of wearing a heavy, awkward device and is thus able to move without restraints. The information transmitted to the cellular telephone or other personal electronic device may then be displayed, processed, stored, employed for local alerts to the user or those persons nearby, or forwarded to another location if needed.

The monitoring system of the present invention monitors a variety of bodily processes, and preferably measures vital signals such as heart rate, blood pressure, respiration rates, etc. The present invention may also be used to monitor glucose levels in diabetic users. Further, the device may be used as an alert system to alert the person and third parties when a person experiences an adverse medical condition.

The medical sensor of the present invention can be any type of thin, lightweight, flexible sensor that is placed inside or on the patient or user's body. The sensors may be either non-invasive or invasive technologies depending on the monitoring needs of the user or patient. Examples of such technology are chips, patches, wristbands or glasses with incorporated sensor arrays. Sensors may be located on any part of a patient's body, such as wrist, chest, head, etc. The sensors may monitor heart conditions, pulse rate, blood pressure, electrical signals, pressure signals or other vital signals.

In one embodiment, sensors may be in the form of glasses. Light emitting diodes emit light into the human temple, while photodiodes capture light reflected back from pulsing blood. The amount of reflected light corresponds to pulse rate, due to blood vessels' expansion during each heartbeat. The signals from the glasses' sensors may be sent directly to an adjacent cellular telephone or a cellular telephone or other personal electronic device where circuitry cleans, amplifies, compares and processes the signal. This information may then be displayed, further processed, stored, used to generate alerts or forwarded to a remote location by the cellular telephone or other personal electronic device. Heart conditions or other adverse medical conditions may be diagnosed and alerted so that the user or remote third party can take appropriate action.

A small short-range transmitter in the sensor sends data from the sensor to the cellular telephone or other personal electronic device, carried by or close by the user, through the use of wireless, radio frequency, infrared or other technology. The sensors and transmitters may be powered by various means, such as solar power, batteries, capacitors, super miniature capacitors, or other power sources. Existing power technology for medical implants is evolving quickly, with many power sources combining high energy density, nearly limitless life and a safe solid-state packaging. These power sources may be placed on the skin or within the body. These power sources may remain indefinitely and be recharged by non-invasive RF energy. These technologies are incorporated into the present invention.

In one embodiment the present invention incorporates an electromagnetic coil in the sensor system for transmitting data and tuning a capacitor and charging a capacitor or battery. The entire device is encapsulated in a biocompatible enclosure, e.g. silicon glass. A passive RF unit, similar to a remote switch controller, is operated at specified frequencies and is activated by moving a cellular telephone or other personal electronic device or a similar device to within approximately a few inches of the sensor. Bringing the cellular telephone or other personal electronic device close to the sensor excites the electromagnetic coil and "wakes up" the sensor. The sensor then begins monitoring vital signals and sending data to the cellular telephone or other personal electronic device.

In a hospital or institution, a cellular telephone or other electronic device may be left close to a patient or passed close to a patient. The sensor-transmitters continuously or periodically transmit the data to the device, which continuously or periodically reports data and status and identification from the sensors and the device to a remote device. Normal readings may be transmitted periodically, as well as instantaneous out of range alert signals. Periods may be seconds or microseconds. Sensing and transmitting occurs in microseconds.

A main advantage of the present invention is the moving of heavy, awkward electronics off the patient's body and into the close by cellular telephone or other electronic device. The sensor array uses only a minimal amount of space and power to read sensed information signals. The bulk of the processing and other processes are performed at the cellular telephone or other personal electronic device.

A receiver in a cellular telephone or other personal electronic device receives and processes the information. Cellular telephones or other personal electronic devices include, but are not limited to, cellular phones, laptop computers, medical monitoring glasses and small handheld processors with transmitters or cellular telephones, including Palm Pilots. The cellular telephone or other personal electronic device functions to display, process, store and forward data from the sensors. Baseline information relating to an individual patient may be input into the cellular telephone or other personal electronic device. Cellular telephones or other personal electronic devices generally have buttons or other input means that allow a user to input information. Furthermore, cellular telephones or other personal electronic devices also have independent power supplies that can power both the traditional functions of the device and the new monitoring system of the present invention. Additionally, adverse medical condition data may also be input to the cellular telephone or other personal electronic device to compare to the data from the sensor. The cellular telephone or other personal electronic device continuously compares the baseline and adverse medical condition data to the information received from the sensor.

If the signals from the transmitter indicate that an adverse medical condition is occurring, the cellular telephone or other personal electronic device alerts the patient and/or remote third parties. Third parties are identified via the wireless technology of the cellular telephone or other personal electronic device. Third parties may include family members, doctors, or emergency medical personnel. A display on the cellular telephone or other personal electronic device gives the patient information about the adverse medical condition and may also instruct the patient regarding appropriate action. If the cellular telephone or other personal electronic device is a cellular phone, the phone may ring, vibrate or otherwise alert the patient or to user inform the patient or user of the occurrence of a dangerous condition with spoken sounds or displays or both.

Blood glucose levels may be monitored through the use of a sensor that incorporates wireless technology. A sensor array, such as light emitting diodes, micro lasers or photo sensors, monitor glucose levels in a blood stream. The sensor array is preferably small, approximately ½" by ½" or smaller. The sensor is placed anywhere on the body and collects interstitial fluid from micro pores created by micro lasers or light emitting diodes in the dead surface layer of the skin. Interstitial fluid is the clear liquid found under the skin and contains concentrations of glucose similar to those found in blood. Therefore, by making known adjustments and corrections, measurements of interstitial fluid give accurate and consistent measurements of glucose levels in the blood. The sensor reads vital signals by using specially designed, light software. The sensor uses a microchip transmitter to transmit information wirelessly to a nearby personal electronic device, such as a cellular phone, laptop computer, Palm Pilot, or other similar device. The cellular telephone or other personal electronic device then displays, processes, stores and forwards the information to another location.

Other methods of monitoring glucose levels are possible. In another glucose measuring embodiment, a device is implanted under the skin. The device contains a biometric sensor that reads temperature, glucose levels, blood pressure, and/or pulse rate. To read glucose levels, the implanted device employs enzymes, such as glucose oxidase enzyme. The enzymes react by producing a voltage proportional to glucose levels.

In another glucose measuring embodiment, a device is placed in contact with a urine sample. The device includes an electrode made of platinum or a similar material on a quartz substrate. The platinum electrode is then coated with special membranes containing glucose oxidase enzyme. When the coated device is placed in contact with the urine sample, glucose in the urine is converted into hydrogen peroxide by the GOE. The hydrogen peroxide then decomposes on the electrodes at certain applied voltage. This creates an electric current proportional to the glucose concentration in the urine sample. The data is then sent to a cellular telephone or other personal electronic device.

While the monitoring system of the present invention may be manufactured as a separate system, it may also be incorporated into existing systems. Off the shelf components may be used to retrofit new hardware into existing cellular telephones or other personal electronic devices. Large capital investments are not required to retool the manufacture of currently available cellular phone circuitry. The hardware of the present invention may be incorporated into the existing structure of the cellular phones.

These and further and other objects and features of the invention are apparent in the disclosure, which includes the above and ongoing written specification, with the claims and the drawings.

DETAILED DESCRIPTION OF THE PREFERRED EMBODIMENTS

The present invention integrates medical monitoring technologies with wireless networks to wirelessly send signals from a monitoring device on a patient to a cellular telephone or other personal electronic device (PED). A thin, lightweight, flexible sensor is placed inside or on the patient's body. Information from the monitoring sensor is transmitted by wireless or infrared technology to a nearby and/or remote cellular telephone or other personal electronic device. By placing the heavier, bulkier components of the monitoring system in the cellular telephone or other personal electronic device, the patient is freed from the restriction of wearing a heavy, awkward device and is thus able to move without restraints. The information transmitted to the cellular telephone or other personal electronic device may then be displayed, processed, stored or forwarded to another location if needed.

The monitoring system of the present invention monitors a variety of bodily processes, but preferably measures vital signals such as heart rate, blood pressure, respiration rates, etc. The present invention may also be used to monitor glucose levels in diabetic users. Further, the device may be used as an alert system to alert the patient and third parties when a patient experiences an adverse medical condition.

Figure 1:
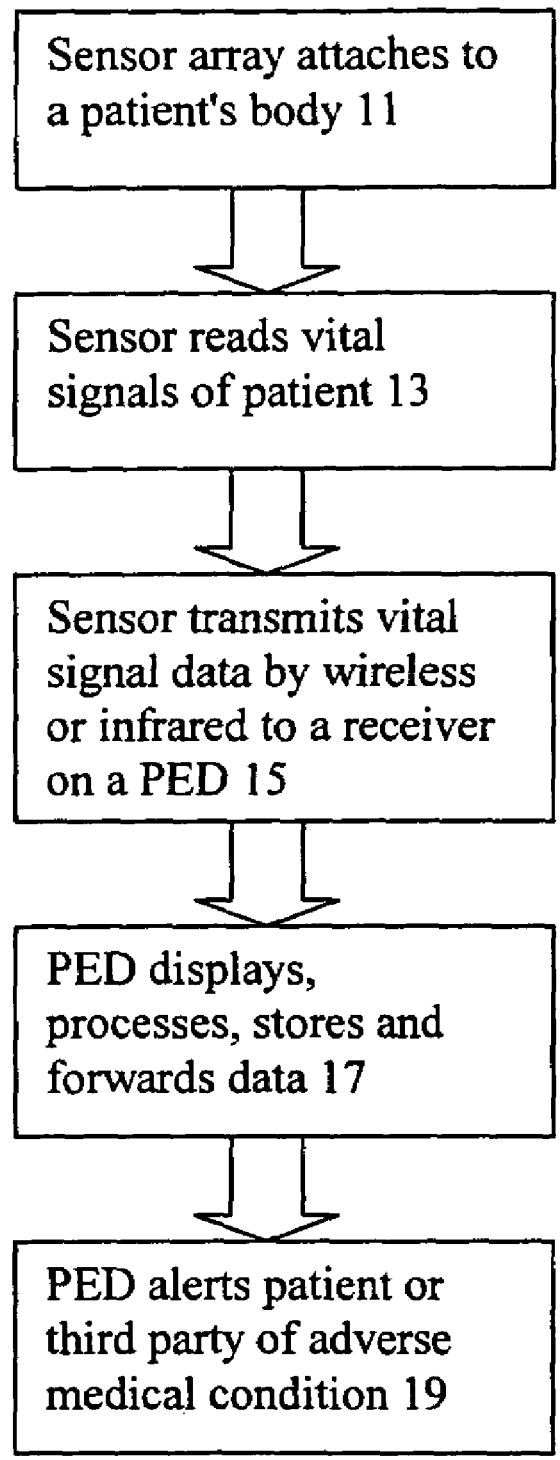
FIG. 1 is a flowchart of the operation of the medical monitoring system.

FIG. 1 shows a method of medical monitoring of the present invention. First, a sensor is attached to a patient's body 11. The sensor then reads the vital signals of the patient 13. The sensor then transmits data by wireless or infrared to a cellular telephone or other personal electronic device 15. The cellular telephone or other personal electronic device then displays, processes, stores and forwards data 17. Finally, if necessary, the cellular telephone or other personal electronic device alerts the patient or a third party of an adverse medical condition 19.

Figure 2:
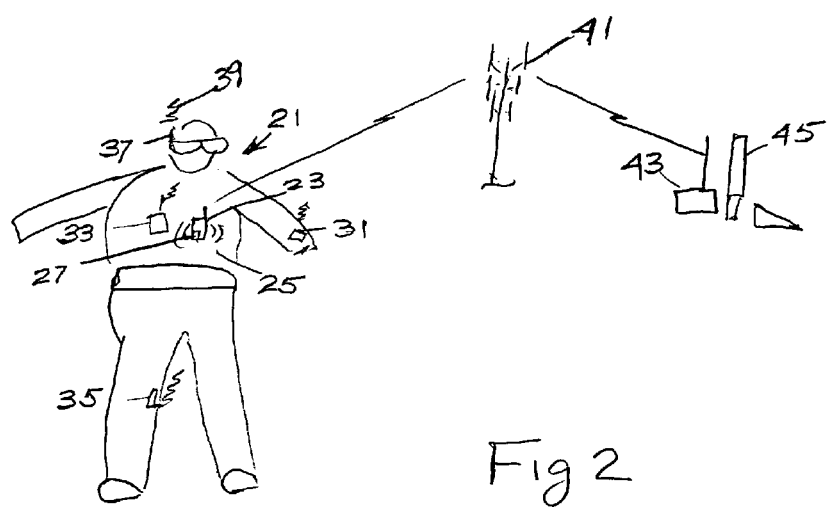
FIG. 2 is a schematic representation of a user with weakly transmitting sensors, and a cell phone which activates the sensors, receives, amplifies, processes, compares and records data, and creates alerts and reports to a remote station.

Referring to FIG. 2, a user 21 carries a cell phone 23 in a pocket 25. The cell phone has circuits 27, which periodically query sensors 31, 33, 35, 37. The sensors receive weak data transmission signals 39, which are broadcast in microsecond spurts of information. The signals provide identification of the sensor and sensed information that is converted to data signals by a sensor contained chip with a transmitter. Each sensor chip includes a receiver circuit for receiving the keying signals to download data timers and memory of time signals and sensed changes, such as pulses per millisecond intervals. The sensors include receivers for receiving data and instructions from the cellular phone or other personal electronic device. Instructions may include starting sensing, stopping sensing, transmitting data or other commands.

Alternatively, all sensors may be wired to a single transmitter for transmitting weak sensor identification and data signals to the cell phone or other personal electronic device circuit. The cell phone circuit stores information and compares received information with preset ranges and outputs of range signals as alerts to ring or vibrate the cell phone and provide audible or visible alerts, and to dial and transmit the specific alerts over cellular transmission networks 41 to another cellular telephone equipped receiver 43, which displays 45 the transmitted information. Periodically, regular data is transferred from cell phones 23 to receivers 43 to indicate circuits in the cell phone and in the sensors are still in operational condition. Preferably, the cell phone queries the sensors concurrently. Batteries or capacitors in the sensor circuits are recharged by power from the cell phone. The queries may be periodic, for example, every few or several seconds. Data transfers are in microsecond bursts. Out of range anomalies are transmitted to the cell phone upon sensing by the sensors.

Figure 3:
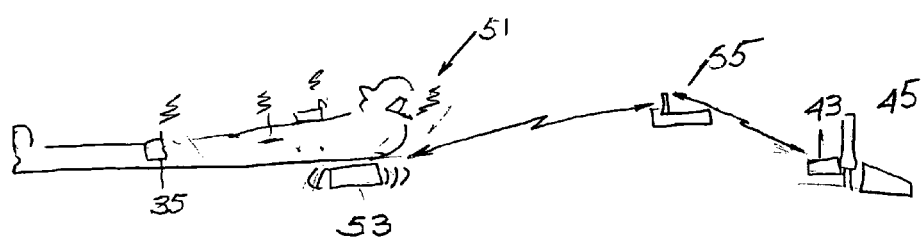
FIG. 3 is a schematic representation of a patient or user with transmitting or wired sensors and a nearby electronic device, which activates the sensors, receives, amplifies, processes, compares and records data, and creates alerts and reports to a remote station via a router and Internet, intranet or cellular telephone communications.

Referring to FIG. 3, a patient 51 has several sensors 31, 33, 35, 37. A local device 53 remains near the patient and periodically queries the sensors. The device contains circuits that activate the sensors, receive, amplify, process, compare and record data, and create alerts and report to a remote station via a router and Internet, intranet or cellular telephone communications. The circuits transmit alerts and periodically transmit sensor and system operating status signals via a local area network to a router 55 and via an intranet or Internet to a receiver 43, which displays 45 the information and alerts a medical assistant, technician or physician.

The medical sensor of the present invention can be any type of thin, lightweight, flexible sensor that is placed inside or on the patient's body. The sensors may be either non-invasive or invasive technologies depending on the monitoring needs of the patient. Examples of such technology are chips, patches, wristbands or glasses with incorporated sensor arrays. Sensors may be located on any part of a patient's body, such as wrist, chest, head, etc. The sensors may monitor heart conditions, pulse rate, blood pressure, electrical signals, pressure signals or other vital signals.

In one embodiment, sensors may be in the form of glasses. Light emitting diodes emit light into the human temple, while photodiodes capture light reflected back from pulsing blood. The amount of reflected light corresponds to pulse rate due to blood vessels' expansion during each heartbeat. The signals from the glasses' sensors may be sent directly to a cellular telephone or other personal electronic device where circuitry cleans, amplifies and processes the signal. This information may then be displayed, further processed, stored or forwarded to a remote location by the cellular telephone or other personal electronic device. Heart conditions or other adverse medical conditions may be diagnosed and the user or remote third party can take appropriate action.

A transmitter in the sensor sends data from the sensor to the cellular telephone or other personal electronic device through the use of wireless or infrared technology. The sensors and transmitters may be powered by various means, such as solar power, batteries, capacitors, super mini capacitors, or other power sources. Existing power technology for medical implants is evolving quickly, with many power sources combining high energy density, nearly limitless life and a safe solid-state packaging. These power sources may be placed on the skin or within the body. These power sources may remain indefinitely and be recharged by non-invasive RF energy. These technologies are incorporated into the present invention.

A main advantage of the present invention is the moving of heavy, awkward electronics off the patient's body and into the cellular telephone or other personal electronic device. The sensor array uses only a minimal amount of space and power to read signals. The bulk of the processing and other processes are performed at the cellular telephone or other personal electronic device.

A receiver in a cellular telephone or other personal electronic device receives and processes the information. Cellular telephones or other personal electronic devices include, but are not limited to, cellular phones, laptop computers, medical monitoring glasses and Palm Pilots. The cellular telephone or other personal electronic device functions to display, process, store, and forward data from the sensors. Baseline information relating to an individual patient may be input into the cellular telephone or other personal electronic device. Cellular telephones or other personal electronic devices generally have buttons or other input means that allow a user to input information. Furthermore, cellular telephones or other personal electronic devices also have independent power supplies that can power both the traditional functions of the device and the new monitoring system of the present invention. Additionally, adverse medical condition data may also be input to the cellular telephone or other personal electronic device to compare to the data from the sensor. The cellular telephone or other personal electronic device continuously compares the baseline and adverse medical condition data to the information received from the sensor.

If the signals from the transmitter indicate that an adverse medical condition is occurring, the cellular telephone or other personal electronic device alerts the patient and/or remote third parties. Third parties are identified via the wireless technology of the cellular telephone or other personal electronic device. Third parties may include family members, doctors, or emergency medical personnel. A display on the cellular telephone or other personal electronic device gives the patient information about the adverse medical condition and may also instruct the patient regarding appropriate action. If the cellular telephone or other personal electronic device is a cellular phone, the phone may ring, vibrate or otherwise inform the patient of the occurrence of a dangerous condition.

Blood glucose levels may be monitored through the use of a sensor that incorporates wireless technology. A sensor array, such as light emitting diodes, micro lasers or photo sensors, monitor glucose levels in a blood stream. The sensor array is preferably small, approximately ½" by ½" or smaller. The sensor is placed anywhere on the body and collects interstitial fluid from micro pores created by micro lasers or light emitting diodes in the dead surface layer of the skin. Interstitial fluid is the clear liquid found under the skin and contains concentrations of glucose similar to those found in blood. Therefore, by making known adjustments and corrections, measurements of interstitial fluid give accurate and consistent measurements of glucose levels in the blood. The sensor reads vital signals by using specially designed, light software. The sensor uses a microchip transmitter to transmit information wirelessly to a nearby cellular telephone or other personal electronic device, such as a cellular phone, laptop computer, palm pilot, or other similar device. The cellular telephone or other personal electronic device then displays, processes, stores and forwards the information to another location.

Other methods of monitoring glucose levels are possible. In another glucose measuring embodiment, a device is implanted under the skin. The device contains a biometric sensor that reads temperature, glucose levels, blood pressure, and/or pulse rate. To read glucose levels, the implanted device employs enzymes, such as glucose oxidase enzyme. The enzymes react by producing a voltage proportional to glucose levels.

In another glucose measuring embodiment, a device is placed in contact with a urine sample. The device includes an electrode made of platinum or a similar material on a quartz substrate. The platinum electrode is then coated with special membranes containing glucose oxidase enzyme. When the coated device is placed in contact with the urine sample, glucose in the urine is converted into hydrogen peroxide by the GOE. The hydrogen peroxide then decomposes on the electrodes at certain applied voltage. This creates an electric current proportional to the glucose concentration in the urine sample. The data is then sent to a cellular telephone or other personal electronic device.

An example of the use of the present medical monitoring device includes the monitoring of a child by parents. A child with diabetes, heart problems or other adverse medical conditions wears a sensor array. When a transient medical condition occurs the transmitter signals the parent's cellular telephone or other personal electronic device. The cellular telephone or ocher personal electronic device displays information about the transient event, thus notifying the parents of any problem.

A similar monitoring scheme may be used for elderly or any other patients.

While the monitoring system of the present invention may be manufactured as a separate system, it may also be incorporated into existing systems. Off the shelf components may be used to retrofit new hardware into existing cellular telephones or other personal electronic devices. Large capital investments are not required to retool the manufacture of currently available cellular phone circuitry. The hardware of the present invention may be incorporated into the existing structure of the cellular phones.

Figure 4:
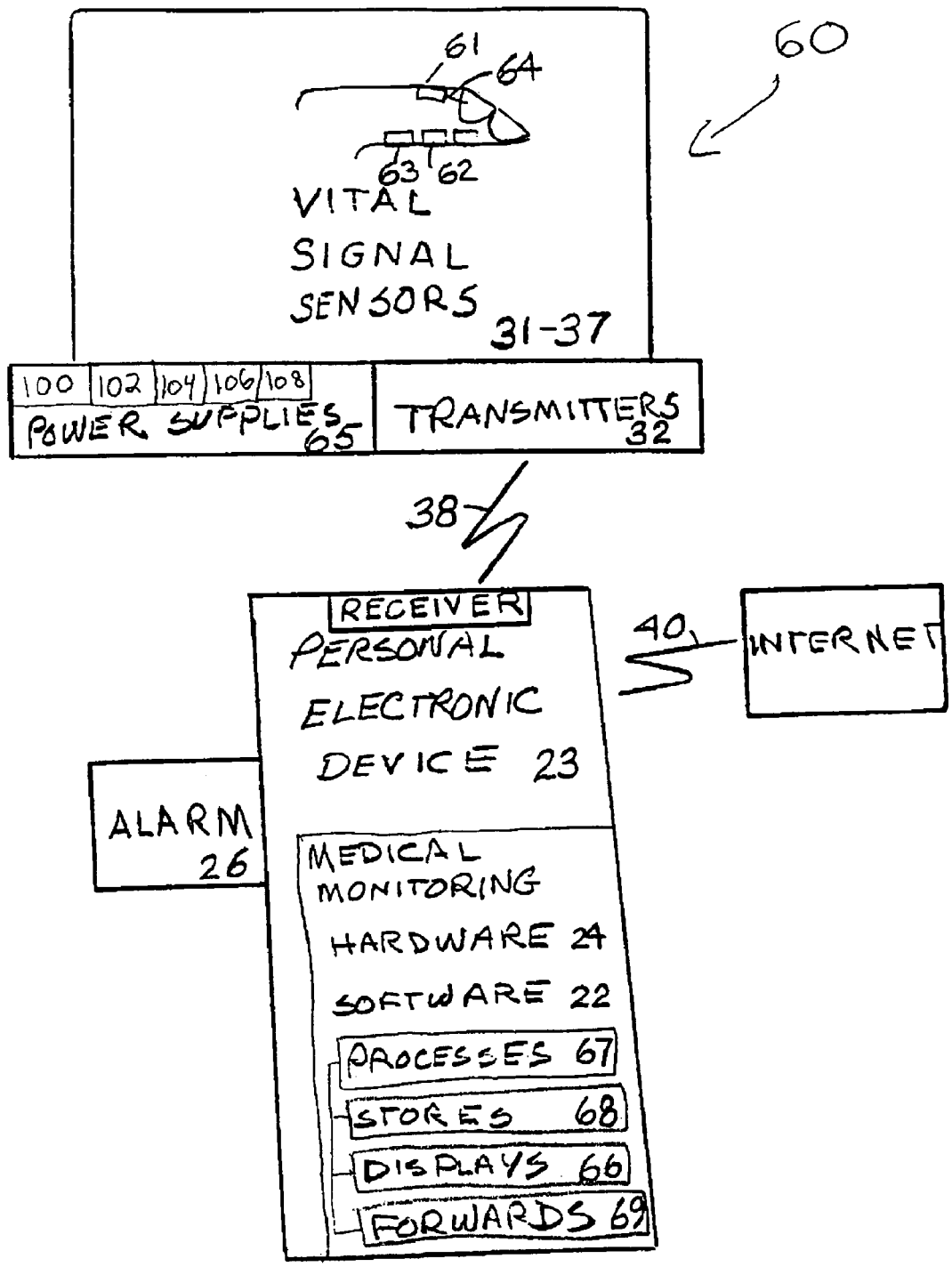
FIG. 4 schematically shows a medical monitoring apparatus.

A medical monitoring apparatus 60 shown in FIG. 4 comprises:

one or more sensors 31 connected to one or more parts of a user's body for reading vital signals, transmitters 32 on the one or more sensors, and a personal electronic device 23, medical monitoring software 22 and hardware 24, alarm devices 26 are in the personal electronic device 23, a wireless or infrared connection 38 between the transmitters 32 and the personal electronic device 23, and a wireless connection 40 between the personal electronic device and the Internet or another wireless device.

The one or more sensors are sensor arrays, chips, patches or wristbands, or one or more sensors are embedded in glasses 61. The glasses emit light 62 into the user's temple and the one or more sensors 63 measure reflected light. The glasses display 64 information in front of the user's eyes.

In an embodiment, the one or more sensors are passive RF units with electromagnetic coils.

The one or more sensors and transmitters are powered by power supplies 65 having solar power, batteries, capacitors, super mini capacitors, RF rechargeable power sources or a combination thereof.

The personal electronic device 23 is a cellular phone, a laptop computer, medical monitoring glasses or a palm pilot.

The personal electronic device displays 66, processes 67, stores 68 and forwards 69 data from the one or more sensors.

An alarm is sounded when data from the one or more sensors reaches or exceeds a predetermined level.

Figure 5:
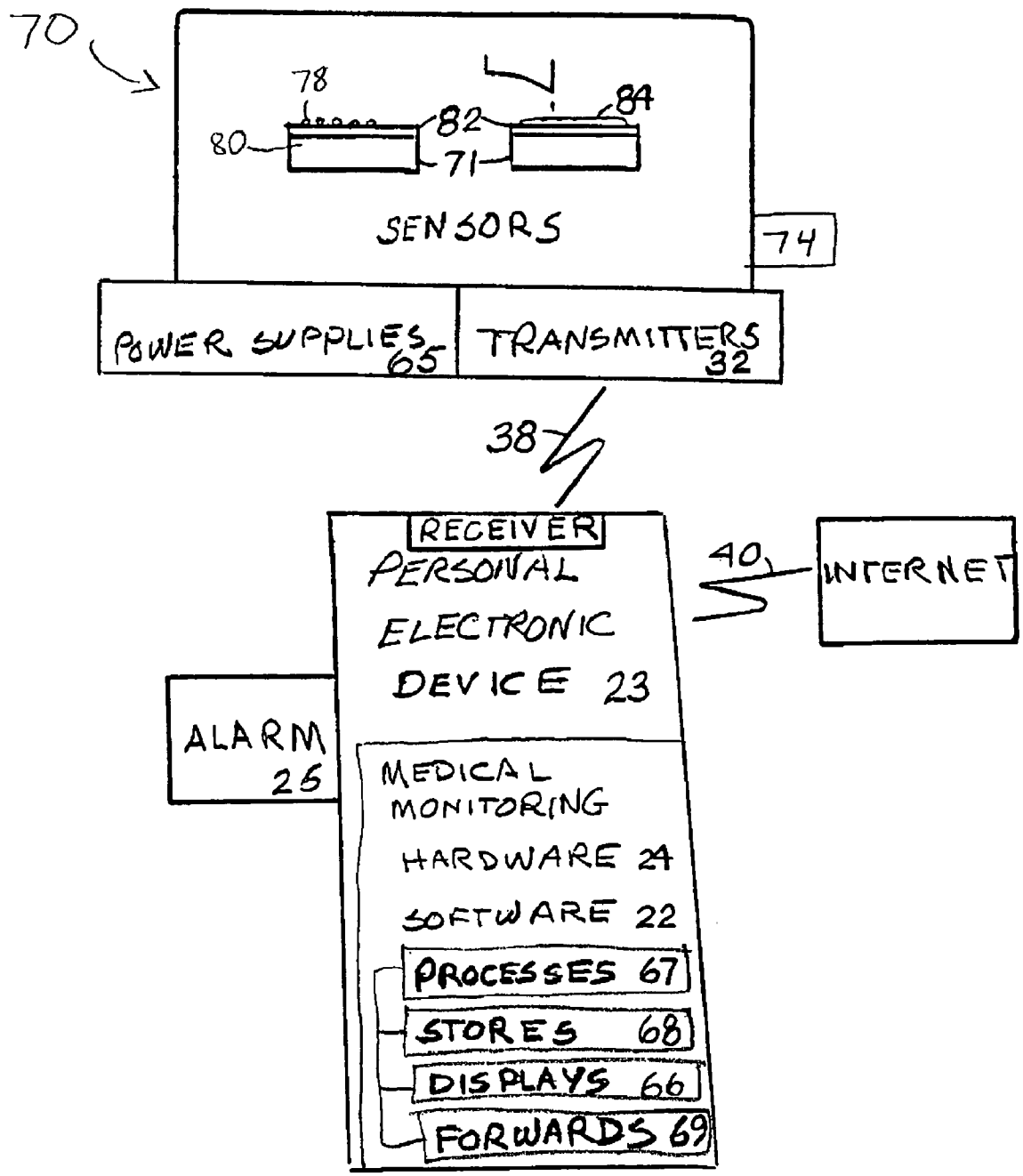
FIG. 5 schematically shows a blood glucose monitoring apparatus.
Figure 6:
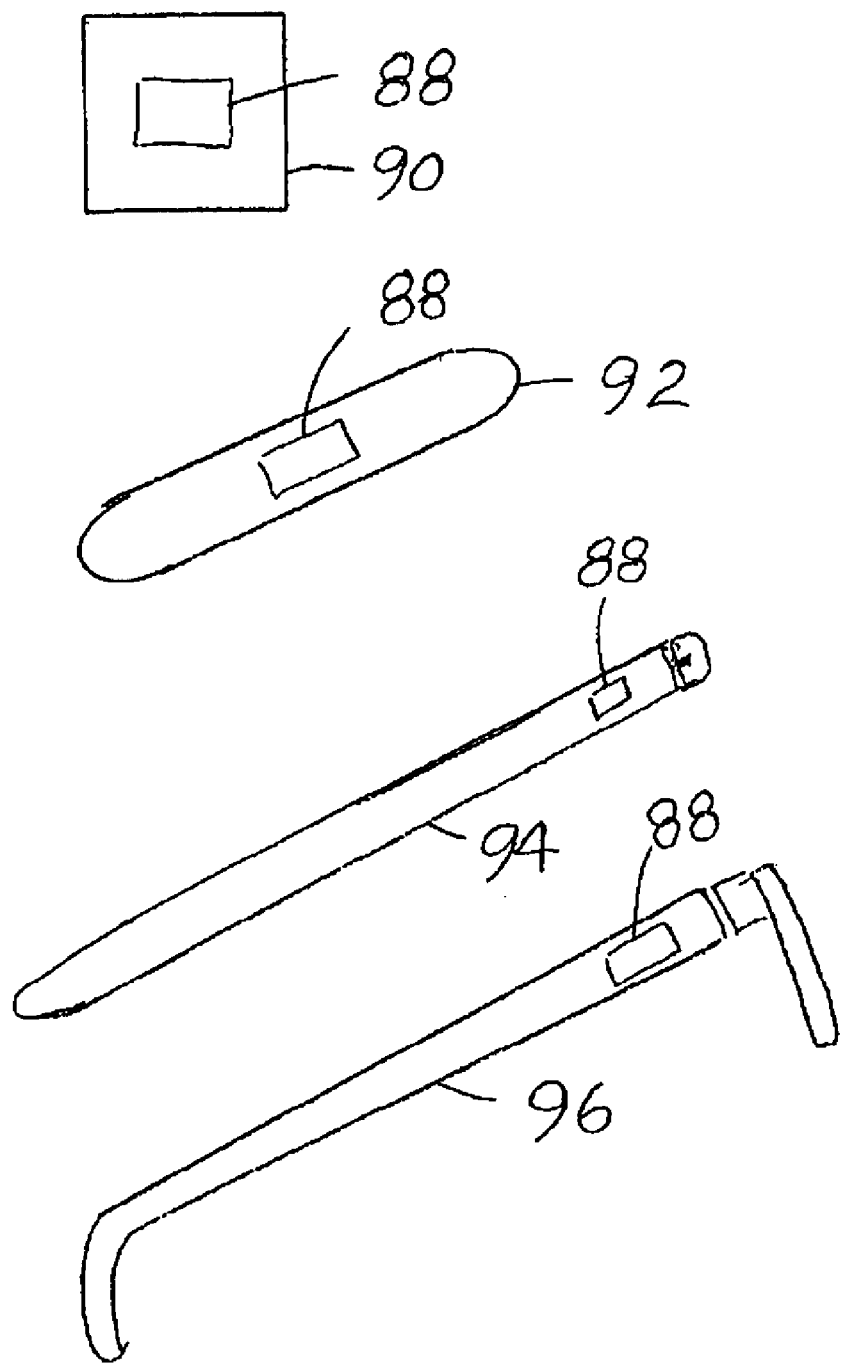
FIG. 6 schematically shows sensors in chips, patches, bands and glasses.
Figure 7:
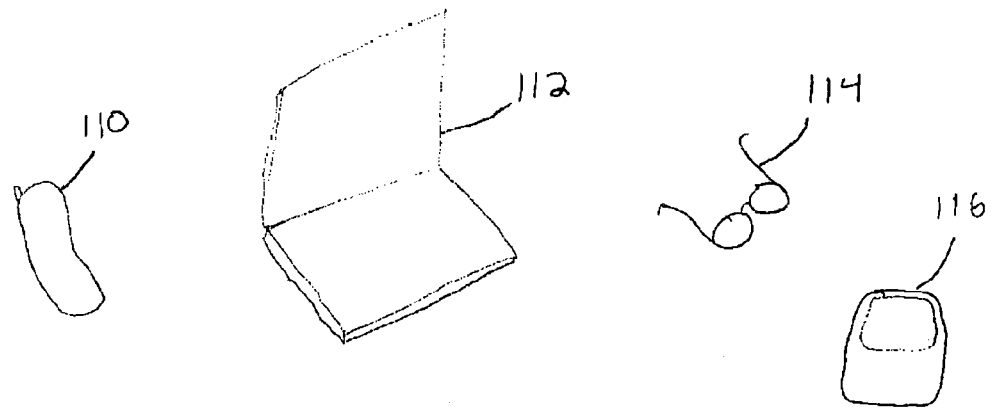
FIG. 7 schematically shows the personal electronic device as a cell phone, laptop, medical monitoring glasses, or a palm pilot.
Figure 8:
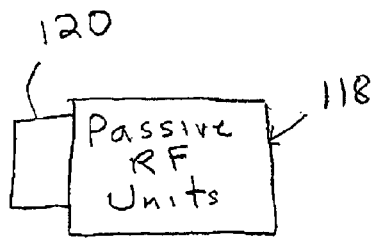
FIG. 8 schematically shows the sensors as passive RF units with electromagnetic coils.
Figure 9:
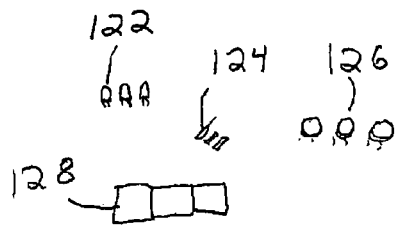
FIG. 9 schematically shows the sensors as LEDs, microlasers, photosensors, or biometric sensors.
Figure 10:
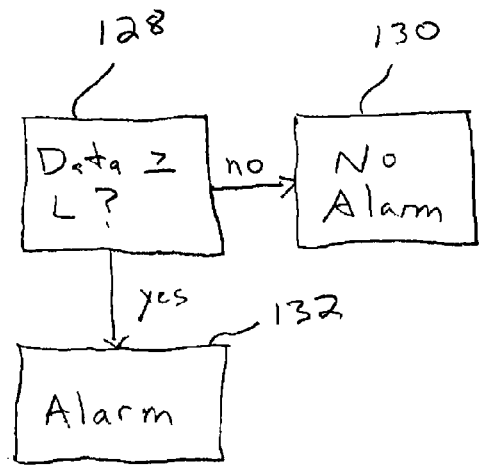
FIG. 10 schematically shows an alarm is triggered only when data reaches or exceeds a predetermined threshold.

A blood glucose monitoring apparatus 70 in FIG. 5 comprises:

one or more sensors 71 for reading blood glucose levels of a user, transmitters 72 on the one or more sensors, a contact 74 between the one or more sensors and the user's body for contacting interstitial fluid, a personal electronic device 23, wherein the personal electronic device comprises medical monitoring software 22 and hardware 24 for displaying, processing, storing and forwarding data, a wireless or infrared connection 38 between the transmitters and a receiver in the personal electronic device, and a wireless connection 40 between the personal electronic device and the Internet or another wireless device.

The one or more sensors are light emitting diodes, micro lasers, photo sensors, or biometric sensors.

Enzymes 76 on the one or more sensors react with glucose and produce a voltage proportional to glucose levels.

Electrodes 78 of platinum or similar materials are on a quartz substrate 80 on the more or more sensors 71, and an enzyme coating 82 on the one or more sensors reacts with glucose and measures glucose concentrations in a urine sample 84 by converting glucose into hydrogen peroxide by the enzyme GOE, decomposing the hydrogen peroxide at the electrodes, and measuring the voltage produced by the decomposing.

While the invention has been described with reference to specific embodiments, modifications and variations of the invention may be constructed without departing from the scope of the invention, which is defined in the following claims.

The invention claimed is:

1. A medical monitoring apparatus comprising:
   plural sensors connected to parts of a user's body for reading vital signals,
   at least one transmitter,
   a personal electronic device,
   medical monitoring software and hardware on the personal electronic device,
   an alarm device on the personal electronic device,
   a wireless or infrared connection between the at least one transmitter and the personal electronic device, and
   a wireless connection between the personal electronic device and the Internet, an intranet or another wireless device,
   wherein the plural sensors are embedded in glasses,
   wherein light emitters on the glasses emit light into the user's temple and the plural sensors receive reflected light, wherein the amount of reflected light corresponds to pulse rate, due to blood vessel expansion during each heartbeat.

2. The apparatus of claim 1, wherein all the sensors are connected to a single transmitter for transmitting weak sensor identification and data signals to the personal electronic device.

3. A method of medical monitoring comprising:
   attaching plural sensors and corresponding transmitters to user's body parts,
   reading vital signals of a user,
   transmitting readings by a wireless or infrared network to a receiver on a personal electronic device,
   displaying, processing, storing and forwarding data with medical monitoring software and hardware on the personal electronic device,
   alerting the user or a third party of an adverse medical condition, and
   transmitting data wirelessly from the personal electronic device to a separate wireless receiver device, intranet or the Internet,
   wherein the plural sensors are passive RF units with an electromagnetic coil, wherein the electromagnetic coil is used to transmit data, tune a capacitor, or charge a capacitor or battery.

4. The method of claim 3, wherein the plural sensors are encapsulated in a biocompatible enclosure.

5. The method of claim 3, wherein the passive RF units are operated at specific frequencies and are activated by moving a personal electronic device to within approximately a few inches of the units.

6. A method of medical monitoring comprising:
   attaching plural sensors and corresponding transmitters to user's body parts,
   reading vital signals of a user,
   transmitting readings by a wireless or infrared network to a receiver on a personal electronic device,
   displaying, processing, storing and forwarding data with medical monitoring software and hardware on the personal electronic device,
   alerting the user or a third party of an adverse medical condition, and
   transmitting data wirelessly from the personal electronic device to a separate wireless receiver device, intranet or the Internet,
   further comprising transmitting instantaneous out-of-range alert signals when the sensors are about to go out of range of the personal electronic device.

7. The method of claim 6, wherein the plural sensors are sensor arrays.

8. The method of claim 6, wherein the plural sensors are in chips, patches and wristbands.

9. The method of claim 6, wherein the plural sensors are embedded in glasses.

10. The method of claim 9, wherein light emitters on the glasses emit light into the user's temple and the plural sensors receive reflected light.

11. The method of claim 6, wherein the plural sensors and transmitters are powered by solar power, batteries, capacitors, super mini capacitors, RF rechargeable power sources or a combination thereof.

12. The method of claim 6, wherein the personal electronic device is a cellular phone, a laptop computer, medical monitoring glasses or a Palm Pilot.

13. The method of claim 6, wherein the alerting occurs when data from the plural sensors reaches or exceeds a predetermined level.

14. The method of claim 6, further comprising diagnosing heart conditions on the personal electronic device.

15. A method of medical monitoring comprising:
   attaching plural sensors and corresponding transmitters to user's body parts,
   reading vital signals of a user,
   transmitting readings by a wireless or infrared network to a receiver on a personal electronic device,
   displaying, processing, storing and forwarding data with medical monitoring software and hardware on the personal electronic device,
   alerting the user or a third party of an adverse medical condition, and
   transmitting data wirelessly from the personal electronic device to a separate wireless receiver device, intranet or the Internet,
   further comprising inputting baseline information relating to an individual patient into the personal electronic device, inputting adverse medical condition data into the personal electronic device, and comparing the baseline and adverse medical condition data to the readings from the sensors.

16. The method of claim 15, wherein the plural sensors are sensor arrays.

17. The method of claim 15, wherein the plural sensors are in chips, patches and wristbands.

18. The method of claim 15, wherein the plural sensors are embedded in glasses.

19. The method of claim 18, wherein light emitters on the glasses emit light into the user's temple and the plural sensors receive reflected light.

20. The method of claim 15, wherein the plural sensors and transmitters are powered by solar power, batteries, capacitors, super mini capacitors, RF rechargeable power sources or a combination thereof.

21. The method of claim 15, wherein the personal electronic device is a cellular phone, a laptop computer, medical monitoring glasses or a Palm Pilot.

22. The method of claim 15, wherein the alerting occurs when data from the plural sensors reaches or exceeds a predetermined level.

23. The method of claim 15, further comprising diagnosing heart conditions on the personal electronic device.

24. A blood glucose monitoring apparatus comprising:
plural sensors for reading blood glucose levels of a user,
transmitters on the plural sensors,
a contact between the plural sensors and the user's body for contacting body interstitial fluid,
a personal electronic device, wherein the personal electronic device comprises medical monitoring software and hardware for displaying, processing, storing and forwarding data,
a wireless or infrared connection between the transmitters and a receiver in the personal electronic device, and
a wireless connection between the personal electronic device and the Internet, an intranet or another wireless device,
wherein the plural sensors are light emitting diodes, micro lasers or photo sensors,
wherein the sensors collect interstitial fluid from micro pores created by micro lasers or light emitting diodes.

25. A medical monitoring apparatus comprising:
plural sensors connected to parts of a user's body for reading vital signals,
at least one transmitter,
a personal electronic device,
medical monitoring software and hardware on the personal electronic device,
an alarm device on the personal electronic device,
a wireless or infrared connection between the at least one transmitter and the personal electronic device, and
a wireless connection between the personal electronic device and the Internet, an intranet or another wireless device,
wherein the sensors further comprise receivers for receiving data and instructions from the personal electronic device, wherein the instructions comprise sensing, stopping sensing, transmitting data, or other commands.

26. The apparatus of claim 25, wherein the plural sensors are sensor arrays.

27. The apparatus of claim 25, wherein the plural sensors are in chips, patches or wristbands.

28. The apparatus of claim 25, wherein the plural sensors and at least one transmitter are powered by solar power, batteries, capacitors, super mini capacitors, RF rechargeable power sources or a combination thereof.

29. The apparatus of claim 28, comprising an RF rechargeable power source, wherein the power source is placed within the body and is recharged by non-invasive RF energy.

30. The apparatus of claim 25, wherein the personal electronic device is a cellular phone, a laptop computer, medical monitoring glasses or a Palm Pilot.

31. The apparatus of claim 30, wherein the personal electronic device displays, processes, stores and forwards data from the plural sensors.

32. The apparatus of claim 25, wherein an alarm is sounded when data from the plural sensors reaches or exceeds a predetermined level.

33. The apparatus of claim 25, wherein all the sensors are connected to a single transmitter for transmitting weak sensor identification and data signals to the personal electronic device.

34. The apparatus of claim 25, wherein the personal electronic device is a cell phone and wherein when the alarm device is activated, an alert is transmitted over a cellular transmission network to another cellular telephone equipped receiver.

35. A method of medical monitoring comprising:
attaching plural sensors and corresponding transmitters to user's body parts,
reading vital signals of a user,
transmitting readings by a wireless or infrared network to a receiver on a personal electronic device,
displaying, processing, storing and forwarding data with medical monitoring software and hardware on the personal electronic device;
alerting the user or a third party of an adverse medical condition, and
transmitting data wirelessly from the personal electronic device to a separate wireless receiver device, intranet or the Internet,
further comprising receiving data transmission signals from the personal electronic device with the sensors, wherein the signals provide identification of the sensor and sensed information.

36. A medical monitoring apparatus comprising:
plural sensors connected to parts of a user's body for reading vital signals,
at least one transmitter,
a personal electronic device,
medical monitoring software and hardware on the personal electronic device,
an alarm device on the personal electronic device,
a wireless or infrared connection between the at least one transmitter and the personal electronic device, and
a wireless connection between the personal electronic device and the Internet, an intranet or another wireless device,
wherein the sensors further comprise receiver circuits for receiving keying signals to download data timers and memory of time signals and sensed changes including pulses per millisecond intervals.

37. A method of medical monitoring comprising:
attaching plural sensors and corresponding transmitters to user's body parts,
reading vital signals of a user,
transmitting readings by a wireless or infrared network to a receiver on a personal electronic device,
displaying, processing, storing and forwarding data with medical monitoring software and hardware on the personal electronic device,
alerting the user or a third party of an adverse medical condition, and
transmitting data wirelessly from the personal electronic device to a separate wireless receiver device, intranet or the Internet,
wherein the personal electronic device is a cell phone, further comprising periodically transferring regular data from the cell phone to the separate wireless receiver device to indicate circuits in the cell phone and in the sensors are still in operational condition.

38. A method of medical monitoring comprising:
attaching plural sensors and corresponding transmitters to user's body parts,
reading vital signals of a user,
transmitting readings by a wireless or infrared network to a receiver on a personal electronic device, displaying, processing, storing and forwarding data with medical monitoring software and hardware on the personal electronic device, alerting the user or a third party of an adverse medical condition, and transmitting data wirelessly from the personal electronic device to a separate wireless receiver device, intranet or the Internet, further comprising recharging batteries or capacitors in the sensors from the portable electronic device.

* * * * *